United States Patent [19]

Ruff et al.

[11] Patent Number: 5,731,000

[45] Date of Patent: *Mar. 24, 1998

[54] STABILIZED PHARMACEUTICAL COMPOSITION CONTAINING BUPROPION

[75] Inventors: Michael David Ruff, Greenville, N.C.; Sanyasi Raju Kalidindi, Edison, N.J.; Joel Elmore Sutton, Jr., Greenville, N.C.

[73] Assignee: Glaxo Wellcome Inc., Rtp, N.C.

[*] Notice: The term of this patent shall not extend beyond the expiration date of Pat. No. 5,358,970.

[21] Appl. No.: 586,916

[22] PCT Filed: Jul. 29, 1994

[86] PCT No.: PCT/GB94/01642

§ 371 Date: Mar. 22, 1996

§ 102(e) Date: Mar. 22, 1996

[87] PCT Pub. No.: WO95/03791

PCT Pub. Date: Feb. 9, 1995

[30] Foreign Application Priority Data

Jul. 30, 1993 [GB] United Kingdom ............... 9315856

[51] Int. Cl.⁶ ................................................. A61K 9/48
[52] U.S. Cl. ..................... 424/451; 424/465; 424/434; 424/476; 424/489; 424/456; 424/453; 424/457
[58] Field of Search ..................... 424/480, 451, 424/493; 514/649

[56] References Cited

U.S. PATENT DOCUMENTS

| | | | |
|---|---|---|---|
| Re. 33,994 | 7/1992 | Baker et al. | 424/465 |
| 3,819,706 | 6/1974 | Mehta | 260/570.5 C |
| 3,885,046 | 5/1975 | Mehta | 424/330 |
| 4,347,176 | 8/1982 | Mehta | 260/112 |
| 4,347,177 | 8/1982 | Phillips | 260/112 B |
| 4,347,178 | 8/1982 | Findlay et al. | 260/112 B |
| 4,347,257 | 8/1982 | Stern | 424/330 |
| 4,347,382 | 8/1982 | Scharver | 564/183 |
| 4,355,179 | 10/1982 | Findlay et al. | 564/177 |
| 4,356,165 | 10/1982 | Findlay | 424/1 |
| 4,393,078 | 7/1983 | Peck | 424/330 |
| 4,425,363 | 1/1984 | Stern | 424/330 |
| 4,435,449 | 3/1984 | Stern | 424/330 |
| 4,438,138 | 3/1984 | Stern | 424/330 |
| 4,507,323 | 3/1985 | Stern | 514/649 |
| 4,571,395 | 2/1986 | Peck | 514/221 |
| 4,687,660 | 8/1987 | Baker et al. | 424/465 |
| 4,769,027 | 9/1988 | Baker et al. | 424/493 |
| 4,798,826 | 1/1989 | Peck | 514/221 |
| 5,358,970 | 10/1994 | Ruff et al. | 514/649 |
| 5,427,798 | 6/1995 | Ludwig et al. | 424/464 |

FOREIGN PATENT DOCUMENTS

| | | |
|---|---|---|
| 0 171 457 A1 | 2/1986 | European Pat. Off. . |
| 0 467 488 A2 | 1/1992 | European Pat. Off. . |
| 2 134 516 | 8/1984 | United Kingdom . |
| WO 92/19226 | 11/1992 | WIPO . |
| WO 94/04138 | 3/1994 | WIPO . |

OTHER PUBLICATIONS

Walters, "Influence of pH on Hydrolytic Decomposition of Diethylopropion Hydrochloride: Stability Studies on Drug"— J. of Phar. Sci. vol. 69, No. 10 (1980).

Laizure, et al. Ther. Drug Monit. 7(4): 447–450 (1985) "Stability of Bupropion" GA. 1040 814822 (1985).

Billinghurst, et al. GA 101:210748e (1985) of U.S. 2 134 516 (Aug. 15, 1984).

Primary Examiner—Thurman K. Page
Assistant Examiner—William E. Benston, Jr.
Attorney, Agent, or Firm—Shah R. Makujina

[57] ABSTRACT

This application discloses a method of inhibiting degradation of the antidepressant bupropion hydrochloride in a solid pharmaceutical formulation, so that the pharmaceutical formulation will maintain at least 80% of its initial bupropion potency after one year.

22 Claims, No Drawings

STABILIZED PHARMACEUTICAL COMPOSITION CONTAINING BUPROPION

The present invention relates to pharmaceutical compositions comprising bupropion hydrochloride and a pharmaceutically acceptable stabiliser and methods of stabilising bupropion hydrochloride in a pharmaceutical composition.

Bupropion hydrochloride is a known antidepressant sold in instant release tablet form under the brand name WELLBUTRIN®. (Also see U.S. Pat. Nos. 3,819,706 and 3,885,046; 1993 Physicians Desk Reference and the Merck Index, Eleventh Edition, Entry No. 1488. Bupropion hydrochloride is also useful as an anticholesterol agent, in suppressing prolactin secretion, in preventing functional impairment and drowsiness seen upon administration of benzodiazepine, in the treatment of minimal brain dysfunction, tardive dyskinesia, impaired mental alertness upon ingestion of ethanol and psychosexual dysfunction. While the instant release tablets currently sold are quite suitable for the indicated use, the method of manufacturing these is less than desirable based on cost as well as process conditions.

The object of the present invention is to prevent (inhibit) the degradation of bupropion hydrochloride, using stabiliser ingredients, thus allowing the preparation of pharmaceutical compositions such as instant and sustained release tablets and capsules which, from a cost of manufacture and processing standpoint, are much improved over those achievable in the past.

Thus the present invention provides a pharmaceutical composition in solid form comprising bupropion hydrochloride and a pharmaceutically acceptable stabiliser in an effective stabilising amount, in which the composition contains at least about 80% w/w of undegraded bupropion hydrochloride after storage for 6 weeks at about 40° C. and 75% relative humidity and in which an aqueous solution of the stabiliser in a concentration of about 6% w/w has a pH of about 0.9 to about 4, the stabiliser being selected from an organic acid, a carboxylic acid, an acid salt of an amino acid and sodium metabisulphite.

Alternatively, the present invention also provides a pharmaceutical composition in solid form comprising bupropion hydrochloride and a pharmaceutically acceptable stabiliser in an effective stabilising mount, in which the composition contains at least about 80% w/w of undegraded bupropion hydrochloride after storage for 6 weeks at about 50° C. and 27% relative humidity and in which an aqueous solution of the stabiliser in a concentration of about 6% w/w has a pH of about 0.9 to about 4, the stabiliser being selected from an organic acid, a carboxylic acid other than ascorbic acid and isoascorbic acid, an acid salt of an amino acid and sodium metabisulphite.

The preferred pH of the aqueous solution of the stabiliser is 0.9 to about 2 and most preferably 1.

Preferably the pharmaceutical composition according to the present invention contains at least about 90% w/w of undegraded bupropion hydrochloride after storage for 6 weeks under the above conditions and more preferably 95% or even 98%. In an additional aspect, the amount of undegraded bupropion hydrochloride is greater than 80% of its labelled strength, and more preferably greater than 90% percent of the labelled strength after one year of storage under the humidity and temperature conditions usually encountered in pharmacies and medicine cabinets i.e. room temperature and 35–60% humidity. Thus, when used in a pharmaceutical preparation for example, a tablet will still retain at least 80% of its potency and preferably at least 90% after one year of storage at room temperature (15°–25° C. (59°–77° F.)) at 35–60% humidity. For example if the tablet initially contains 100 mg bupropion hydrochloride (labelled amount) at time of preparation, after one year storage at least 80 mg of undegraded bupropion hydrochloride will remain in the tablet.

The amount of the stabiliser which may be used with the present invention may vary but preferably is about 2.7% to 27%, most preferably about 5% to 16.2% based on the label strength of bupropion hydrochloride in the pharmaceutical formulation (composition) in solid form. For example if a formulation contains 100 mg of bupropion hydrochloride it would preferably contain about 2.7 to 27 g of stabiliser.

Stabilisers of use in this invention include organic acids, carboxylic acids, acid salts of amino acids and sodium metabisulphite. Preferably, the acid salts of amino acids are hydrochloride salts such as cysteine hydrochloride, glycine hydrochloride or cystine dihydrochloride. Other preferred examples of stabilisers according to the present invention include: ascorbic acid, malic acid, isoascorbic acid, citric acid and tartaric acid. L-cysteine hydrochloride and glycine hydrochloride are the most preferred stabilisers.

In the examples the cysteine hydrochloride is in the L form and NF and USP are designations for standards published in the National Formulary and US Pharmacopeia, respectively.

The present invention extends to the use of combinations of stabilisers especially combinations of the aforementioned stabilisers.

The pH of the aqueous solution of the stabilisers may be determined as follows:

The stabiliser is weighed out to provide 3.75 grams thereof, (except for 3.34 grams of L-cystine dihydrochloride) and is then added to 60 grams of distilled water in a glass Pyrex® beaker. The resulting mixture is stirred for approximately 5 minutes, using a stir plate and magnetic stir bar. The resulting solution or dispersion is examined using either a Orion Model 701A Ionalyzer®, or an Accumet pH Meter Model 915. Solutions are stirred with a magnetic stir bar during analysis. Measurements of pH are performed in triplicate and the average thereof is used.

Examples of forms of preferred solid pharmaceutical composition include a tablet or capsule. Such forms are prepared using standard procedures known in the art which involve admixing buproprion hydrochloride and the stabiliser with the tablet or capsule excipients. Such excipients may include, for example, microcrystalline cellulose, sodium starch glycolate and/or corn starch, talc, magnesium stearate and colloidal silicon dioxide. Caplets are tablets generally shaped in the form of capsules. Capsules of this invention are generally prepared by mixing the stabiliser with bupropion hydrochloride and other excipients and placing same in, e.g., a two-pan hard gelatin capsule.

Preferably the weight of the inactive ingredients is greater than about 1½ times that of bupropion hydrochloride but less than about 4 times that of bupropion hydrochloride. The tablets or capsules of this invention generally contain 25 mg to 500 mg of bupropion hydrochloride and usually contain 50 mg, 75 mg, 100 mg or 150 mg of bupropion hydrochloride. The amount of bupropion hydrochloride in solid form pharmaceutical compositions e.g. tablets after storage, may be determined using standard procedures such as high performance liquid chromatography (HPLC).

This invention is also directed to a new and improved method for stabilising the antidepressant bupropion hydrochloride to prevent the degradation thereof by admixing the stabiliser with bupropion hydrochloride. In this way a pharmaceutical composition is produced in which the bupropion hydrochloride is inhibited from degrading thus facilitating the storage of the composition over a prolonged period of time at room temperature i.e. under humidity and temperature conditions usually encountered in pharmacies and in medicine cabinets.

The compositions according to the present invention include those suitable for oral, rectal, topical (including buccal and sublingual) or transdermal administration.

The compositions may conveniently be presented in unit dosage form and may be prepared by any of the methods well known in the art of pharmacy. All methods include the step of bringing bupropion hydrochloride and the stabiliser into association with a carrier which constitutes one or more accessory ingredients. In general, the composistions are prepared by uniformly and intimately bringing bupropion hydrochloride and the stabiliser into association with a finely divided solid carrier and then, if necessary, shaping the product.

Compositions of the present invention suitable for oral administration may be presented as discrete units such as capsules, cachets, tablets or lozenges, each containing a predetermined amount of bupropion hydrochloride and the stabiliser; as a powder or granules including microencapsulated or time-release forms.

A tablet may be made by compression or molding, optionally with one or more accessory ingredients. Compressed tablets may be prepared by compressing in a suitable machine, bupropion hydrochloride and the pharmaceutically acceptable stabiliser in a free-flowing form such as a powder or granules optionally mixed with a binder, disintegrant, lubricant, inert diluent, surface active agent or dispersing agent. Molded tablets comprising a mixture of the powdered bupropion hydrochloride and the stabiliser with any suitable carrier may be made by molding in a suitable machine.

Compositions suitable for rectal administration may be presented as a suppository with a conventional carrier such as cocoa butter, hydrogenated fats or hydrogenated fatty carboxylic acids.

Compositions suitable for topical administration in the mouth, for example buccally or sublingually, include lozenges comprising bupropion hydrochloride and the stabiliser in a flavoured basis such as sucrose and acacia or tragacanth, and pastilles comprising the active compound in a basis such as gelatin and glycerin or sucrose and acacia.

In addition to the aforementioned ingredients, the compositions of this invention may further include one or more accessory ingredient(s) selected as appropriate from diluents, buffers, flavouring agents, binders, disintegrants, surface active agents, thickeners, lubricants, preservatives (including antioxidants) and the like.

The following examples are representative of the invention.

In the examples, cysteine hydrochloride means L-cysteine hydrochloride.

EXAMPLE 1

The formulation contained the following ingredients in the following amounts:

| Ingredient | 100 mg potency Weight (mg) per tablet | 75 mg potency |
|---|---|---|
| Bupropion hydrochloride | 100.00 | 75.0 |
| Microcrystalline cellulose, NF | 91.3 | 68.5 |
| Sodium starch glycolate, NF | 9.2 | 6.9 |
| L-Cysteine hydrochloride, NF | 5.0 | 3.8 |

-continued

| Ingredient | 100 mg potency Weight (mg) per tablet | 75 mg potency |
|---|---|---|
| Talc, USP | 23.0 | 17.3 |
| Magnesium stearate, NF | 1.2 | 0.9 |
| Colloidal silicon dioxide, NF | 0.3 | 0.2 |
| TOTAL | 230.0 mg | 172.6 mg |

The powder ingredients were weighed out for a 120,000 tablet batch size for the 100 mg potency and a 160,000 tablet batch size for the 75 mg potency.

The bupropion hydrochloride, microcystalline cellulose and sodium starch glycolate were sifted through a 30 mesh Russell-Finex sifter.

The sifted ingredients were blended for 15 minutes in a 3 cu. ft. slant-cone blender.

The blended ingredients were granulated as follows:

The cysteine hydrochloride was dissolved in 1.28 kg of purified water using a Lightnin'® Mixer. This cysteine hydrochloride solution was added to 5.12 kg of SD3A alcohol (anhydrous) and mixed thoroughly using a Lightnin'® Mixer. The blended ingredients were placed in a 3 cu. ft. Littleford Lodige granulator and ganulated using the cysteine hydrochloride solution. Mixing time was 3 to 5 minutes and chopper time was 3 to 5 minutes. Wetness was checked and additional 80% w/w SD3A alcohol (aqueous) solution was added to achieve appropriate massing.

Clumps of wet granule were broken up by hand.

Granule was dried in a WST-30 Glatt fluid-bed dryer until loss on drying (by Compu-Trac®, 90° C.) of granule was between 1 to 2%. Fluid-bed dryer parameters were set as follows:

Inlet air temperature: 60° C.
Air volume: 200–800 cu meter/hr
Pro-heat temperature: 25° C.
Dew point: 10° C.
By-pass flap: 50%
Shaker interval: 5 seconds every. 2 minutes Dried granule was sifted through a 20 mesh Russell-Finex sifter.

Talc (pro-sifted 60 mesh) was added to a small amount of dried granule, sifted through a 20 mesh Russell Finex sifter, added to a 3 cu. ft. slant-cone blender and blended with the remainder of the granule for 5 minutes. Magnesium stearate and colloidal silicon dioxide was sifted together through a 30 mesh Russell-Finex sifter and blended in a table-top v-shell blender for 20 minutes. This magnesium stearate/ colloidal silicon dioxide blend was then added to the dried granule in the 3 cu. ft. slant-cone blender and blended an additional 5 minutes.

The lubricated granule was compressed on a rotary-type Manesty Betapress® in a controlled humidity environment of less than 30% relative humidity. Tablets were compressed at a compression weight of about 230 mg for the 100 mg potency and about 172.6 mg for the 75 mg potency. Round, 7.8 mm. concave, plain punches were used for the 100 mg potency and round, 7.0 mm. concave, plain punches were used for the 75 mg potency.

Tablets were dedusted using a Manesty Tablet Deduster.

A portion of tablets was film-coated using a compu-lab Acella—Cota® film-coater. The aqueous film coat Opadry® Red YS-1-1846 was used for the 100 mg potency and Opadry® Yellow YS-1-2186 for the 75 mg potency (supplied by Colocon, Inc. of 415 Moyer Blvd, West Point, Pa. 19486. The Accela—Cota® parameters were:

Inlet air temperature: 50°–80° C.
Inlet air volume: 100–500 cfm
Exhaust air temperature: 50°–60° C.

Tablets were coated to a weight gain of 1–5% based on the core tablet weight to achieve an acceptable color intensity.

EXAMPLE 2

The procedure of Example 1 was repeated except that lubricant levels were changed, resulting in the following formulation:

| Ingredient | 100 mg potency tablet Weight (mg) per tablet |
|---|---|
| Bupropion hydrochloride | 100.0 |
| Microcrystalline cellulose, NF | 91.3 |
| Sodium starch glycolate, NF | 9.2 |
| L-Cysteine hydrochloride | 5.0 |
| Talc, USP | 23.0 |
| Magnesium stearate, NF | 2.4 |
| Colloidal silicon dioxide, NF | 0.6 |
| TOTAL | 231.5 |

EXAMPLE 3

The procedure of Example 2 was repeated except;

In order to achieve a 75 mg potency, the tablets were compressed using 7.0mm. round, concave, plain punches and were not film-coated. Tablets had the resulting formulation:

| Ingredient | 75 mg potency tablet Weight (mg) per tablet |
|---|---|
| Bupropion hydrochloride | 75.0 |
| Microcrystalline cellulose, NF | 68.5 |
| Sodium starch glycolate, NF | 6.9 |
| L-Cysteine hydrochloride | 3.8 |
| Talc, USP | 17.3 |
| Magnesium stearate, NF | 1.8 |
| Colloidal silicon dioxide, NF | 0.5 |
| TOTAL | 173.8 |

EXAMPLE 4

Tablets are manufactured according to the following formulation:

| Ingredient | 100 mg potency tablet Weight (mg) per tablet |
|---|---|
| Bupropion hydrochloride | 100.0 |
| Microcrystalline cellulose, NF | 91.3 |
| Sodium starch glycolate, NF | 9.2 |
| Glycine hydrochloride | 5.0 |
| Talc, USP | 23.0 |
| Magnesium stearate, NF | 1.2 |
| Colloidal silicon dioxide, NF | 0.32 |
| TOTAL | 230.0 MG |

Sufficient powder ingredients were weighed out to make approximately 24,000 tablets.

The bupropion hydrochloride, microcrystalline cellulose and sodium starch glycolate were sifted through a 30 mesh Kussell-Finex sifter.

The sifted ingredients were blended for 15 minutes in a Patterson-Kelly (PK) v-shell blender.

The blended ingredients were granulated as follows:

A quantity of purified water, USP that equals approximately 25% of the total weight of granulating solvent needed to impart the desired granule wetness was weighed out. The glycine hydrochloride was dissolved in the purified water using a Lightnin'® Mixer. The glycine hydrochloride solution was added to a quantity of SD3A alcohol, anhydrous, equal to the remaining 75% of the total weight of solvent needed to impart the desired granule wetness and mixed thoroughly using a Lightnin'® Mixer. The blended ingredients were placed in a Hobart planetary mixer and granulated using the glycine hydrochloride solution. Mixing and time was approximately 3 to 5 minutes. Granulation wetness was checked and additional 75% w/w SD3A alcohol (aqueous) solution was added to achieve appropriate massing.

Any clumps of wet granule were broken up by hand.

Granule was dried in a Despatch Tray Oven to 50° C. for approximately 4 hours until loss on drying (by Compu-Trac®, 90° C.) of granule was 1 to 2%.

Dried granule was sifted through a 20 mesh Russell-Finex sifter.

Talc (pre-sifted 60 mesh) was added to a small amount of dried granule and sifted through a 20 mesh hand screen. This was added to the remainder of the granule and blended in a PK v-shell blender for 5 minutes. Magnesium stearate and colloidal silicon dioxide was sifted together through a 30 mesh hand screen, and blended in a PK v-shell blender for 15–20 minutes. This magnesium stearate/colloidal silicon dioxide blend was then added to the granule/talc blend in the PK v-shell blender and blended an additional 5 minutes.

The lubricated granule was compressed on a rotary-type Manesty Betapress® in a controlled humidity environment of less than 30% relative humidity. Tablets were compressed at a compression weight of 230 mg, using 7.8 mm. round, concave, plain punches.

EXAMPLE 5

The procedure of Example 4 is repeated except that the lubricant levels are changed resulting in the following formulation:

| Ingredient | 100 mg potency tablet Weight (mg) per tablet |
|---|---|
| Bupropion hydrochloride | 100.0 |
| Microcrystalline cellulose, NF | 91.3 |
| Sodium starch glycolate, NF | 9.2 |
| Glycine hydrochloride | 5.0 |
| Talc, USP | 22.9 |
| Magnesium stearate, NF | 0.7 |
| Colloidal silicon dioxide, NF | 0.2 |
| TOTAL | 229.3 mg |

Tablets are compressed at approximately 229.3 mg.

EXAMPLE 6

The procedure of Example 4 is repeated except that the lubricant levels are changed resulting in the following formulation:

| Ingredient | 100 mg potency tablet Weight (mg) per tablet |
|---|---|
| Bupropion hydrochloride | 100.0 |
| Microcrystalline cellulose, NF | 91.3 |
| Sodium starch glycolate, NF | 9.2 |
| Glycine hydrochloride | 5.0 |
| Talc, USP | 0.9 |
| Magnesium stearate, NF | 1.1 |
| Colloidal silicon dioxide, NF | 0.2 |
| TOTAL | 217.7 mg |

Tablets are compressed at approximately 217.7 mg.

EXAMPLE 7

The procedure of Example 4 was repeated except that the lubricant levels were changed resulting in the following formulation:

| Ingredient | 100 mg potency tablet Weight (mg) per tablet |
|---|---|
| Bupropion hydrochloride | 100.0 |
| Microcrystalline cellulose, NF | 91.3 |
| Sodium starch glycolate, NF | 9.2 |
| Glycine hydrochloride | 5.0 |
| Talc, USP | 10.9 |
| Magnesium stearate, NF | 0.7 |
| Colloidal silicon dioxide, NF | 0.2 |
| TOTAL | 217.3 mg |

Tablets are compressed at approximately 217.3 mg.

EXAMPLE 8

The procedure of Example 4 was repeated except magnesium stearate and colloidal silicon dioxide were replaced with sodium stearyl fumarate resulting in the following formulation:

| Ingredient | 100 mg potency tablet Weight (mg) per tablet |
|---|---|
| Bupropion hydrochloride | 100.0 |
| Microcrystalline cellulose, NF | 91.3 |
| Sodium starch glycolate, NF | 9.2 |
| Glycine hydrochloride | 5.0 |
| Talc, USP | 10.9 |
| Sodium stearyl fumarate | 3.3 |
| TOTAL | 219.7 mg |

Tablets are compressed at approximately 219.7 mg.

EXAMPLE 9

The procedure of Example 4 was repeated except the formulation is changed as follows:

| Ingredient | 100 mg potency tablet Weight (mg) per tablet |
|---|---|
| Bupropion hydrochloride | 100.0 |
| Microcrystalline cellulose, NF | 68.8 |
| Corn starch, NF | 23.0 |
| Sodium starch glycolate, NF | 9.2 |
| Glycine hydrochloride | 5.0 |
| Talc, USP | 23.0 |
| Magnesium stearate, NF | 0.8 |
| Colloidal silicon dioxide, NF | 0.2 |
| TOTAL | 230.0 mg |

Tablets are compressed at approximately 230.0 mg.

EXAMPLE 10

The procedure of Example 4 is repeated except sodium starch glycolate is replaced with crospovidone, resulting in the following formulation:

| Ingredient | 100 mg potency tablet Weight (mg) per tablet |
|---|---|
| Bupropion hydrochloride | 100.0 |
| Microcrystalline cellulose, NF | 95.9 |
| Crospovidone | 4.6 |
| Glycine hydrochloride | 5.0 |
| Talc, USP | 23.0 |
| Magnesium stearate, NF | 1.2 |
| Colloidal silicon dioxide, NF | 0.3 |
| TOTAL | 230.0 mg |

Tablets are compressed at approximately 230.0 mg.

EXAMPLE 11

The procedure of Example 4 is repeated except that the formulation is changed as follows:

| Ingredient | 100 mg potency tablet Weight (mg) per tablet |
|---|---|
| Bupropion hydrochloride | 100.0 |
| Microcrystalline cellulose, NF | 68.8 |
| Corn starch, NF | 23.0 |
| Sodium starch glycolate, NF | 9.2 |
| L-Cysteine hydrochloride | 5.0 |
| Talc, USP | 23.0 |
| Magnesium stearate, NF | 1.2 |
| Colloidal silicon dioxide, NF | 0.3 |
| TOTAL | 230.5 mg |

Tablets were compressed at approximately 230.5 mg.

EXAMPLE 12

The procedure of Example 11 is repeated except that L-cysteine hydrochloride is replaced with glycine hydrochloride.

The procedure of Example 4 is repeated except that the sodium starch glycolate and colloidal silicon dioxide are removed and the formulation follows:

| Ingredient | 100 mg potency tablet Weight (mg) per tablet |
|---|---|
| Bupropion hydrochloride | 100.0 |
| Microcrystalline cellulose, NF | 71.0 |

-continued

| Ingredient | 100 mg potency tablet Weight (mg) per tablet |
|---|---|
| Corn starch, NF | 22.0 |
| L-Cysteine hydrochloride | 5.0 |
| Talc, USP | 22.0 |
| Magnesium stearate, NF | 1.1 |
| TOTAL | 221.1 mg |

Tablets were compressed at approximately 221.1 mg.

EXAMPLE 14

The procedure of Example 4 was repeated except that the sodium starch glycolate was removed and the formulation follows:

| Ingredient | 100 mg potency tablet Weight (mg) per tablet |
|---|---|
| Bupropion hydrochloride | 100.0 |
| Microcrystalline cellulose, NF | 71.0 |
| Corn starch, NF | 22.0 |
| L-Cysteine hydrochloride | 5.0 |
| Talc, USP | 22.0 |
| Magnesium stearate, NF | 1.1 |
| Colloidal silicon dioxide, NF | 0.2 |
| TOTAL | 221.3 mg |

Tablets were compressed at approximately 221.3 mg.

A portion of tablets was film-coated using a Compu-Lab Accela-Cota® film-coater.

The aqueous film coat Opadry Red YS-1-1846 was used for the 100 mg potency. The Acella-Cota® parameters were:
Inlet air temperature: 50°–80° C.
Inlet air volume: 200–1000 cfm
Exhaust air temperature: 40°–60° C.
Exhaust air volume: 200–1000 cfm Tablets were coated to a weight gain of 1–5% over the core tablet weight to achieve an acceptable color intensity.

150 MG CAPSULES

EXAMPLE 15

150 mg capsules were prepared according to the following formulation and procedure:

| | Weight (mg) per capsule |
|---|---|
| Bupropion hydrochloride | 150.0 |
| Microcrystalline cellulose, NF | 106.5 |
| Corn starch, NF | 33.00 |
| Talc, USP | 33.00 |
| L-Cystein hydrochloride | 7.500 |
| TOTAL | 330.0 mg |

A stock blend of bupropion hydrochloride, corn starch (purity 826) and microcrystalline cellulose (MCC) was prepared as follows:

The above ingredients were sifted by hand through a 30 mesh screen. They were then blended in an Patterson-Kelly (P-K) v-shell blender for 10 minutes.

The proper amount of cysteine hydrochloride was weighed out and added to 85% w/w SD3A alcohol (aqueous) solution. This mixture was vigorously mixed for approximately 5 minutes. It was then immediately added to the proper amount of the above mentioned stock blend and wet-granulated in a table-top Hobart mixer.

The resulting wet granulation was screened by hand through a 16 mesh screen.

The wet granule was dried in a tray oven at 50° C. for 4 hours to obtain a loss on drying (LOD) of below 2% using a CompuTrac® moisture analyser 90° C. (Upon standing the batches re-equilibrated to 2–3% LOD).

The dried granule was sifted through a 16 or 30 mesh hand screen.

The granule was lubricated with talc (sifted 60 mesh), in a P-K v-shell blender for 5 minutes.

Finished granule is encapsulated on a Chemi-Pharm manual capsule-filling machine Model No. 201, using size No. 1, white, opaque two part hard gelatin capsules.

EXAMPLE 16

The procedure of Example 15 is repeated except cysteine hydrochloride was replaced with glycine hydrochloride.

EXAMPLE 17

The procedure of Example 15 is repeated except cysteine hydrochloride was replaced with L-cystine dihydrochloride.

EXAMPLE 18

The procedure of Example 15 is repeated except cysteine hydrochloride was replaced with tartaric acid.

EXAMPLE 19

The procedure of Example 15 is repeated except cysteine hydrochloride was replaced with citric acid.

EXAMPLE 20

The procedure of Example 15 is repeated except cysteine hydrochloride was replaced with malic acid.

EXAMPLE 21

The procedure of Example 15 is repeated except cysteine hydrochloride is replaced with isoascorbic (erythorbic) acid.

EXAMPLE 22

The procedure of Example 15 is repeated except cysteine hydrochloride is replaced with ascorbic acid.

EXAMPLE 23

The procedure of Example 15 is repeated except cysteine hydrochloride is replaced with sodium metabisulfite.

CAPLETS

EXAMPLE 24

The caplets were manufactured according to the following formulation:

| Ingredient | 100 mg potency caplet Weight (mg) per caplet |
|---|---|
| (Core) | |
| Bupropion hydrochloride | 100.0 |
| Microcrystalline cellulose, NF | 274.0 |
| Sodium starch glycolate, NF | 15.00 |
| L-Cysteine hydrochloride, USP | 9.00 |
| Talc, USP | 12.00 |
| Magnesium stearate, NF | 4.00 |
| CORE WEIGHT | 414.0 MG |
| (Coating) | |
| Opadry® Red. YS-1-1846 | 12.00 |
| Carnauba Wax NF | 0.04 |
| TOTAL WEIGHT | 426.0 |

Sufficient powder ingredients were weighed out to make a batch size of approximately 60,000 caplets.

The bupropion hydrochloride, microcrystalline cellulose and sodium starch glycolate were sifted through a 20 or 30 mesh Russell Finex sifter.

The sifted ingredients were blended for 15 minutes in a 3 cu. ft. slant-cone blender.

The blended ingredients were granulated as follows:

A quantity of purified water, USP that equals approximately no more than 20% of the total weight of granulating solution needed to impart the desired granule wetness was weighed out. The cysteine hydrochloride was dissolved in the purified water using a mixer. The cysteine hydrochloride solution was added to a quantity of SD3A alcohol, anhydrous, equal to the remaining 80% (no less than) of the total weight of solution needed to impart the desired granule wetness and mixed thoroughly using a mixer. The blended ingredients were placed in a 3 cu. ft. Littleford Lodige® granulator and granulated using the hydroalcoholic cysteine hydrochloride solution. Mixing and chopper time was approximately 5–10 minutes. Wetness was checked and additional 80% w/w SD3A alcohol (aqueous) solution was added to achieve appropriate massing.

Any clumps of wet granule were broken up by hand.

Granule was dried in a WST-30 Glatt fluid-bed dryer until loss on drying (by Compu-Trac®, 90° C.) of granule was 0.8–2.0%. Fluid-bed drying parameters were set as follows:
Inlet air temperature: 60° C.
Air volume: 200–1200 cu meter/hr Dried granule was milled using a Comil® and appropriately sized screen.

Talc Gore-sifted 60 mesh) was added to small amount of dried granule and mixed by hand. Magnesium stearate Gore-sifted) was added to a small amount of dried granule and mixed by hand. Both mixtures were sifted through a 16 mesh screen in a Russell Finex sifter. This sifted mixture was added to the remainder of the granule and blended in the 3 cu. ft slant-cone blender for 5 minutes.

The lubricated granule was compressed on a rotary-type Manesty Betapress®. Caplets were compressed at a compression weight of approximately 414 gm. using 6.5×14.5 mm concave, caplet punches containing a partial score-bar on the upper and lower punches.

Caplets were dedusted using a Manesty Tablet Deduster.

A portion of tablets was film-coated using a Compu-Lab Accela-Cota® film-coater. The aqueous film coat Opadry Red® YS-1-1846 was used. The Accela-Cota® parameters were:

Inlet air temperature: 50°–80° C.
Inlet air volume: 100–500 cfm
Exhaust air temperature: 40°–60° C.

Caplets were coated to a weight gain of 1–5% over the core tablet weight to achieve an acceptable color intensity.

Caplets were coated with carnauba wax to assist in packaging. Carnauba wax was added to the film-coated caplets which were rotated in the coating drum for approximately 5 minutes to distribute the wax.

EXAMPLE 25

The procedure of Example 24 is repeated except:

In order to achieve a 75 mg potency, the caplets are compressed at a compression weight of approximately 310.5 mg, using 5.9×13.1 mm concave, caplet punches containing a partial score-bar on the upper and lower punches. The aqueous film coat Opadry® Yellow-Gold YS-1-2186 is for the 75 mg potency. Caplets have the resulting composition:

| Ingredient | 75 mg potency caplet Weight (mg) per caplet |
|---|---|
| (Core) | |
| Bupropion hydrochloride | 75.00 |
| Microcrystalline cellulose, NF | 205.5 |
| Sodium starch glycolate, NF | 11.25 |
| Cysteine hydrochloride, USP | 6.750 |
| Talc, USP | 9.00 |
| Magnesium stearate, NF | 3.00 |
| CORE WEIGHT | 310.5 mg |
| (Coating) | |
| Opadry Yellow, YS–1-2186 | 9.00 |
| Carnauba Wax, NF | 0.03 |
| TOTAL WEIGHT | 319.50 mg |

EXAMPLE 26

The procedure of Example 24 is repeated except:

In order to achieve a 50 mg potency, the caplets are compressed at a compression weight of approximately 207 mg, using 5.1×11.4 mm concave, caplet punches containing a partial scorebar on the upper and lower punches. The aqueous film coat Opadry® White YS-1-7059 is used for the 50 mg potency. Caplets have the resulting composition:

| Ingredient | 50 mg potency caplet Weight (mg) per caplet |
|---|---|
| (Core) | |
| Bupropion hydrochloride | 50.00 |
| Microcrystalline cellulose, NF | 137.0 |
| Sodium starch glycolate, NF | 7.50 |
| Cysteine hydrochloride, USP | 4.50 |
| Talc, USP | 6.00 |
| Magnesium stearate, NF | 2.00 |
| CORE WEIGHT | 207.0 mg |
| (Coating) | |
| Opadry White ®, YS-1-7059 | 6.00 |
| Carnauba Wax, NF | 0.02 |
| TOTAL WEIGHT | 213.0 mg |

EXAMPLE 27

The procedure of Example 24 is repeated except:

The blended powders are granulated with 100% SD3A Alcohol.

EXAMPLE 28

The procedure of Example 27 is repeated except:

The cysteine hydrochloride is blended in dry with the other ingredients rather than adding it to the granulating solution.

The level of cysteine hydrochloride is increased giving the caplets the following composition:

| Ingredient | 100 mg potency caplet Weight (mg) per caplet |
|---|---|
| Bupropion hydrochloride | 100.00 |
| Microcrystalline cellulose, NF | 274.0 |
| Sodium starch glycolate, NF | 15.00 |
| Cysteine hydrochloride, USP | 18.00 |
| Talc, USP | 12.00 |
| Magnesium stearate, NF | 4.00 |
| CORE WEIGHT (Coating) | 423.0 mg |
| Opadry Red ®, YS-1-1846 | 12.00 |
| Carnauba Wax, NF | 0.040 |
| TOTAL WEIGHT | 435.0 mg |

EXAMPLE 29

The procedure of Example 24 was followed except:

Glycine hydrochloride is used as the Stabiliser, giving the caplets the following composition:

| Ingredient | 100 mg potency caplet Weight (mg) per caplet |
|---|---|
| Bupropion hydrochloride | 100.00 |
| Microcrystalline cellulose, NF | 274.0 |
| Sodium starch glycolate, NF | 15.00 |
| Glycine hydrochloride, USP | 9.00 |
| Talc, USP | 12.00 |
| Magnesium stearate, NF | 4.00 |
| CORE WEIGHT (Coating) | 414.0 mg |
| Opadry Red ®, YS-1-1846 | 12.00 |
| Carnauba Wax, NF | 0.04 |
| TOTAL WEIGHT | 426.0 mg |

EXAMPLE 30

The procedure of Example 24 was repeated except:

The blended powders were granulated with 100% Isopropyl alcohol.

We claim:

1. A pharmaceutical composition in solid form comprising bupropion hydrochloride and a pharmaceutically acceptable stabiliser in an effective stabilising mount, in which the composition contains at least about 80% w/w of undegraded bupropion hydrochloride after storage for 6 weeks at about 40° C. and 75% relative humidity and in which an aqueous solution of the stabiliser in a concentration of about 6% w/w has a pH of about 0.9 to about 4, the stabiliser being selected from an organic acid, a carboxylic acid, an acid salt of an amino acid and sodium metabisulphite.

2. A pharmaceutical composition in solid form comprising bupropion hydrochloride and a pharmaceutically acceptable stabiliser in an effective stabilising mount, in which the composition contains at least about 80% w/w of undegraded bupropion hydrochloride after storage for 6 weeks at about 50° C. and 27% relative humidity and in which an aqueous solution of the stabiliser in a concentration of about 6% w/w has a pH of about 0.9 to about 4, the stabiliser being selected from an organic acid, a carboxylic acid other than ascorbic acid and isoascorbic acid, an acid salt of an amino acid and sodium metabisulphite.

3. A pharmaceutical composition according to claim 1, wherein the aqueous solution of the stabiliser has a pH of about 0.9 to 2.

4. A pharmaceutical composition according to claim 1, wherein the aqueous solution of the stabiliser has a pH of around 1.

5. A pharmaceutical composition according to claim 1 which contains at least 95% w/w of undegraded bupropion hydrochloride.

6. A pharmaceutical composition according to claim 1, wherein the amount of stabiliser is 2.7% to 27% of the weight of bupropion hydrochloride in the composition.

7. A pharmaceutical composition according to claim 2, wherein the amount of stabiliser is 5% to 16.2% of the weight of bupropion hydrochloride in the composition.

8. A pharmaceutical composition according to claim 1, wherein the acid salt of the amino acid is cysteine hydrochloride, glycine hydrochloride or cystine dihydrochloride.

9. A pharmaceutical composition according to claim 1, wherein the organic acid is tartaric acid, citric acid or malic acid.

10. A pharmaceutical composition according to claim 1 wherein the carboxylic acid is ascorbic acid or isoascorbic acid.

11. A tablet or capsule according to claim 1, wherein the mount of bupropion hydrochloride is 50, 75, 100 or 150 mg.

12. A method of stabilising bupropion hydrochloride in a solid pharmaceutical composition so that at least about 80% w/w of bupropion hydrochloride is present in the undegraded form after storage for 6 weeks at about 40° C. and 75% relative humidity, wherein said method comprises mixing bupropion hydrochloride with a stabiliser of which an aqueous solution in a concentration of about 6% w/w has a pH of about 0.9 to about 4, the stabiliser being selected from an organic acid, a carboxylic acid, an acid salt of an amino acid and sodium metabisulfite.

13. A method of stabilising bupropion hydrochloride in a solid pharmaceutical composition so that at least about 80% w/w of bupropion hydrochloride is present in the undegraded from after storage for 6 weeks at about 50° C. and 27% relative humidity, wherein said method comprises mixing bupropion hydrochloride with a stabiliser of which an aqueous solution in a concentration of about 6% w/w has a pH of about 0.9 to about 4, the stabiliser being selected from an organic acid, a carboxylic acid other than ascorbic acid or isoascrobic acid, an acid salt of an amino acid and sodium metabisulfite.

14. A pharmaceutical composition according to claim 2, wherein the aqueous solution of the stabiliser has a pH of about 0.9 to 2.

15. A pharmaceutical composition according to claim 2, wherein the aqueous solution of the stabiliser has a pH of around 1.

16. A pharmaceutical composition according to claim 2 which contains at least 95% w/w of undegraded bupropion hydrochloride.

17. A pharmaceutical composition according to claim 2, wherein the acid salt of the acid is cysteine hydrochloride, glycine hydrochloride or cystine dihydrochloride.

18. A pharmaceutical composition according to claim 2, wherein the organic acid is tartaric acid, citric acid or malic acid.

19. A pharmaceutical composition according to claim 2 wherein the carboxylic acid is ascorbic acid or isoascorbic acid.

20. A tablet or capsule according to claim 2, wherein the amount of bupropion hydrochloride is 50, 75, 100 or 150 mg.

21. A pharmaceutical composition according to claim 1, wherein the aqueous solution of the stabiliser has a pH of about 0.9 to 2;

the composition contains at least 95% w/w of undegraded bupropion hydrochloride;

the amount of stabiliser is 2.7% to 27% of the weight of bupropion hydrochloride in the composition;

the acid salt of the amino acid is cysteine hydrochloride, glycine hydrochloride or cystine dihydrochloride;

the organic acid is tartaric acid, citric acid or malic acid;

the carboxylic acid is ascorbic acid or isoascorbic acid; and wherein the amount of bupropion hydrochloride is 50, 75, 100 or 150 mg.

22. A pharmaceutical composition according to claim 2, wherein the aqueous solution of the stabiliser has a pH of about 0.9 to 2;

the composition contains at least 95% w/w of undegraded bupropion hydrochloride;

the amount of stabiliser is 2.7% to 27% of the weight of bupropion hydrochloride in the composition;

the acid salt of the amino acid is cysteine hydrochloride, glycine hydrochloride or cystine dihydrochloride;

the organic acid is tartaric acid, citric acid or malic acid;

the carboxylic acid is ascorbic acid or isoascorbic acid; and wherein the amount of bupropion hydrochloride is 50, 75, 100 or 150 mg.

* * * * *